United States Patent
Worzewski

(10) Patent No.: US 6,192,274 B1
(45) Date of Patent: Feb. 20, 2001

(54) TWO-CHAMBER PACEMAKER

(75) Inventor: Wolf Worzewski, Berlin (DE)

(73) Assignee: Biotronik Mess-und Therapiegerate GmbH & Co. IngenieurbUro Berlin, Berlin (DE)

(*) Notice: Under 35 U.S.C. 154(b), the term of this patent shall be extended for 0 days.

(21) Appl. No.: 09/333,659

(22) Filed: Jun. 16, 1999

(30) Foreign Application Priority Data

Jun. 16, 1998 (DE) .............................................. 198 27 807

(51) Int. Cl.$^7$ .................................................. A61N 1/362
(52) U.S. Cl. ........................................................... 607/14
(58) Field of Search .......................................... 607/9, 14

(56) References Cited

U.S. PATENT DOCUMENTS

| 5,167,224 | 12/1992 | Limousin et al. |
| 5,253,644 | 10/1993 | Elmvist . |
| 5,496,350 | 3/1996 | Lu . |
| 5,507,783 | 4/1996 | Buchanan . |
| 5,549,648 | 8/1996 | Stoop . |
| 5,653,738 | 8/1997 | Sholder . |

FOREIGN PATENT DOCUMENTS

| 0 077 808 | 8/1987 | (EP) . |
| 0 308 535 | 3/1989 | (EP) . |
| 0 677 304 | 10/1995 | (EP) . |
| 0 726 082 | 8/1996 | (EP) . |

Primary Examiner—William E. Kamm
(74) Attorney, Agent, or Firm—Venable; Robert Kinberg

(57) ABSTRACT

Two-chamber pacemaker (100), comprising atrium sensing means (EA, 107) as well as ventricle sensing means (EV, 105) and refractory switching means (100B) for influencing the processing of output signals from the atrium sensing means for a predetermined refractory time, further comprising ventricle stimulation means (106, EV) and a stimulation control unit (100A), which effects a changeover back from a non-atrium synchronous 1:1 operating mode to an atrium-synchronous 1:1 operating mode in dependence on the signals from the atrium sensing means that are influenced by the refractory switching means. A signal pattern memory is provided in this case for storing a signal sequence pattern, which reflects a predetermined sequence of heart activities, a signal sequence memory for storing a sequence of output signals from the atrium and the ventricle sensing means, comparator means for comparing the sequence of output signals to the stored signal sequence pattern and for emitting an output signal if the two coincide, as well as refractory changeover means for adjusting a shortened refractory time for the refractory switching means in dependence on the output signal from the comparator means.

10 Claims, 2 Drawing Sheets

TWO-CHAMBER PACEMAKER

Figure 1:
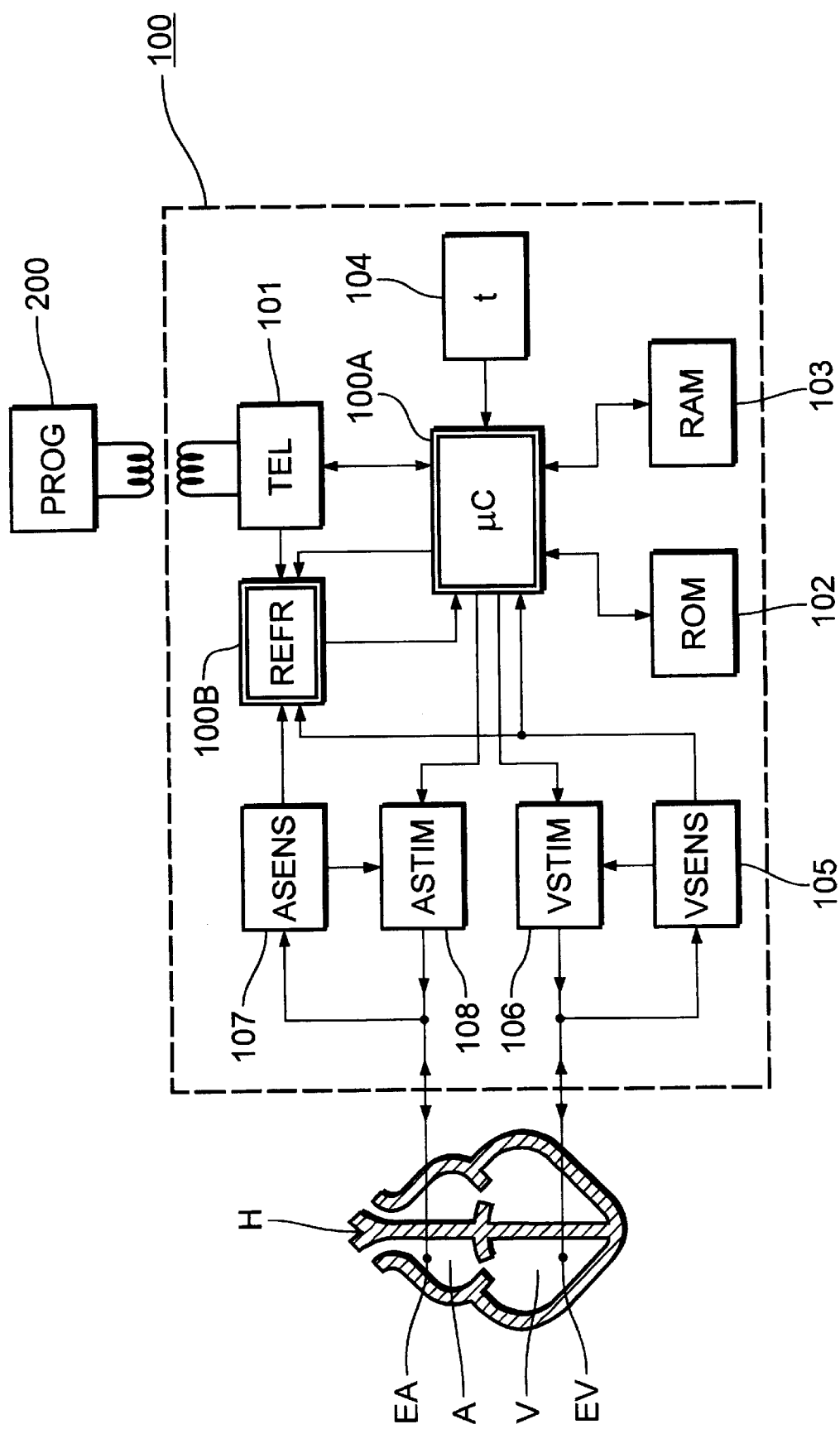

The invention relates to a two-chamber pacemaker according to the preamble to claim 1.

Two-chamber pacemakers have long been known and have proven themselves in the treatment of multiple cases of arrhythmia. However, despite the meanwhile extensive experience gained in the use of these devices, the clinical use of these pacemakers still poses certain problems.

One of the best known and most important problems is the danger of pacemaker-induced tachycardias:

An increase in the ventriculoatrial conduction must be expected following the occurrence of ventricular extrasystoles in the clinical sense (in the following called "clinical VES") because the chamber depolarization was not preceded by an atrial depolarization and the ventriculoatrial conduction path (here in particular of the AV nodes) is therefore not refractory. If this physiological condition is not considered when designing the pacemaker timing, a pacemaker-induced tachycardia (PMT) can result following a clinical VES. Such a tachycardia develops in that following the clinical VES, a p-wave formed by retrograde conduction is detected outside of a post-ventricular atrial refractory period (post-ventricular ARP or also "PVARP") that is adjusted on the pacemaker, which then triggers a chamber pulse. As a result, the retrograde p-wave following this chamber pulse is detected and triggers a chamber pulse and so forth.

To prevent the triggering of a pacemaker-induced tachycardia following a clinical VES after a ventricular sensory event, identified by the pacemaker as VES, a PVARP must be started that is longer than the (assumed) VA conduction time following the clinical VES and thus also lasts longer than the normal PVARP following a ventricular sensory event that is not identified as VES. Compare also the EP-B-0 077 808 in this connection.

All pacemaker manufacturers use the missing AV synchronicity of the ventricular sensory event as recognition criterion for a clinical VES. It means that any ventricular-sensed event, which was not preceded by an atrial event (atrial sensory event outside of the ARP or atrial pace event), is considered a ventricular extrasystole by the pacemaker. Such an extrasystole—quasi defined via the perception capacity of the pacemaker—is also referred to as a "pacemaker VES." This previously mentioned VES recognition criterion has a high sensitivity. That is to say, with intact ventricular perception without interference signals, all occurring clinical VES also manifest themselves as pacemaker VES. However, the specificity of the recognition criterion is lower, meaning not all pacemaker VES are also actually clinical VES.

In the case of an atrium depolarization, which is conducted into the chamber and is perceived therein, an incorrect evaluation can occur, for example, if the atrium depolarization did not start an AV time because it was either not perceived in the atrium at all or it was perceived within the ARP and therefore did not become effective for the pacemaker control. Such an atrium depolarization is also called a "refractory A-sensory event." If such an A-sensory event is conducted into the heart chamber, the ventricular sensory event is rated as pacemaker VES and triggers a prolonged PVARP. With respect to this, compare also the EP-A-0 308 535.

If the inherent atrial frequency in addition is sufficiently high and/or the PR interval is relatively long, the subsequent p-wave falls within the extended PVARP and is not detected or at the very least is not used for the pacemaker control. It means that not every atrial action is followed by an atrium-synchronous chamber stimulation. This mode of operation of the pacemaker is referred to in the following as "pacemaker VES behavior." A special case is the function of the 2:1 blockage, where a chamber stimulus follows only after each second atrial action. This mode of operation continues until the RP interval is shorter than the extended PVARP, started by the pacemaker VES. However, as soon as a p-wave arrives outside of the extended PVARP, an AV time is started and the chamber is again atrium-synchronous stimulated.

An atrium-synchronous stimulation of the chamber at a ratio of 1:1 occurs, for example, if a patient with a known two-chamber pacemaker and a PR interval of 200 ms for a PVARP of 200 ms and an AV time<200 ms has an inherent atrial frequency (rate)<150/min, meaning a chamber pulse follows each p-wave. If the atrial rate exceeds a threshold value (in the following also called an "entrance threshold") of 150/min at the onset of an atrial tachycardia, the aforementioned pacemaker VES behavior occurs and the PVARP is extended to 400 ms. However, if the atrial rate falls once more below the entrance threshold, the pacemaker does not immediately return to the atrium-synchronous operation, but returns to it only if the RP interval reaches>400 ms. In the example, this is the case only for an atrial rate of<100/min, meaning if the rate falls below a second threshold value (in the following also referred to as "exit threshold"). Only then does the p-wave respectively arrive outside of the extended PVARP, which is started by a pacemaker VES.

Thus, the return from the pacemaker VES behavior to the atrium-synchronous operation during the disappearance of an atrial tachycardia is delayed longer, meaning the exit threshold is lower, the longer the time interval for which the extended PVARP was adjusted and/or the longer the PR interval. A comparable problem occurs with two-chamber pacemakers where the AV time can be adjusted to match the currently valid stimulation rate and for which a longer AV time is valid in the region of the 2:1 blockage behavior than outside of this operational mode. For this, compare also the EP-A-0 726 082. An equally comparable problem occurs with pacemakers having a so-called total atrial refractory period (TARP), which normally starts with the A-sensory event or, if such an event does not occur, with the following V-sensory event (pacemaker VES).

This pacemaker behavior can lead to ECG interpretation problems because an atrium-synchronous chamber stimulation does not (yet) occur at atrial rate values, for which such a stimulation is expected. A longer-lasting pacemaker VES behavior is physiologically a disadvantage for the patient, specifically in the case of a hypertrophic, obstructive cardiomyopathy or a symptomatic AV blockage 1.

Thus, it is the object of the invention to create a two-chamber pacemaker with improved response behavior during the dying out of an atrial tachycardia, which pacemaker does not require a considerable increase in expenditure for the realization.

This object is solved with a two-chamber pacemaker having the features as stated in claim 1.

The invention incorporates the idea of making it possible to return to the atrium-synchronous chamber stimulation while the p-waves are still detected as refractory A sensory event. If a predetermined number of event sequences are detected, involving a ventricular sensory event, followed by a refractory A sensory event, followed by a ventricular sensory event, followed by a refractory A sensory event, etc., the ARP is clearly shortened as a test for at least one operating cycle. This is designed to allow the pacemaker to return to the 1:1 atrium-synchronous chamber stimulation, specifically if the actual atrial rate is below the aforementioned entrance threshold, but still above the exit threshold.

For this, a predetermined succession of signal sequence patterns that mirror the heart activities—namely based on the above pattern $(Vs-Asref)_n$ in a predetermined number n of repeat actions—is stored (programmed) in a signal pattern memory, while the actual sequence of output signals of the atrial and the ventricular sensory means is recorded during the 1:1 non-synchronous operation in a signal sequence memory, and a comparison is made in a comparator to compare the sequence of output signals with the stored signal sequence pattern. Finally, if the result of the comparison is positive, refractory time changeover means serve to adjust a shortened refractory time for the refractory switching means, in dependence on the output signal from the comparator.

The signal pattern memory can be designed for storing a basic sequence and can be supplemented by an n-counter or can be designed from the start for storing n sequences. Corresponding to the signal pattern storage means, the signal sequence memory is designed to store a number of output signals from the atrial and ventricular sensing means that correspond to the length of the signal sequence pattern.

The refractory switching means of an additional, advantageous variant of the invention comprise a refractory time memory with at least two storage areas for storing different refractory times, wherein respectively two memory areas can be accessed selectively with the aid of the refractory changeover means. However, more than two refractory times or refractory time pairs can be stored as well, to permit a patient-individual selection at the implanted device by means of a programming device. As an alternative, the refractory time changeover means can comprise a divider stage, which can be used to vary at a fixed ratio a preprogrammed normal refractory time for the test.

The length of the signal sequence pattern can be programmed for the signal pattern storage means (or a counter assigned thereto), and the number of output signals to be evaluated over a telemetric distance can be programmed correspondingly for the signal sequence memory.

The refractory switching means in particular are designed (in a manner known per se) so as to form a combination refractory time from a basic refractory time and an extension value ("ARP extension"), which is added in the event that a refractory time is started by a signal from the ventricular sensing means.

For an advantageous use of the invention in a pacemaker with adaptation of the AV time to the rate, the refractory switching means—also in a manner known per se—are designed to establish the refractory time in dependence on a detected frequency of the activity in the atrium.

Figure 2:
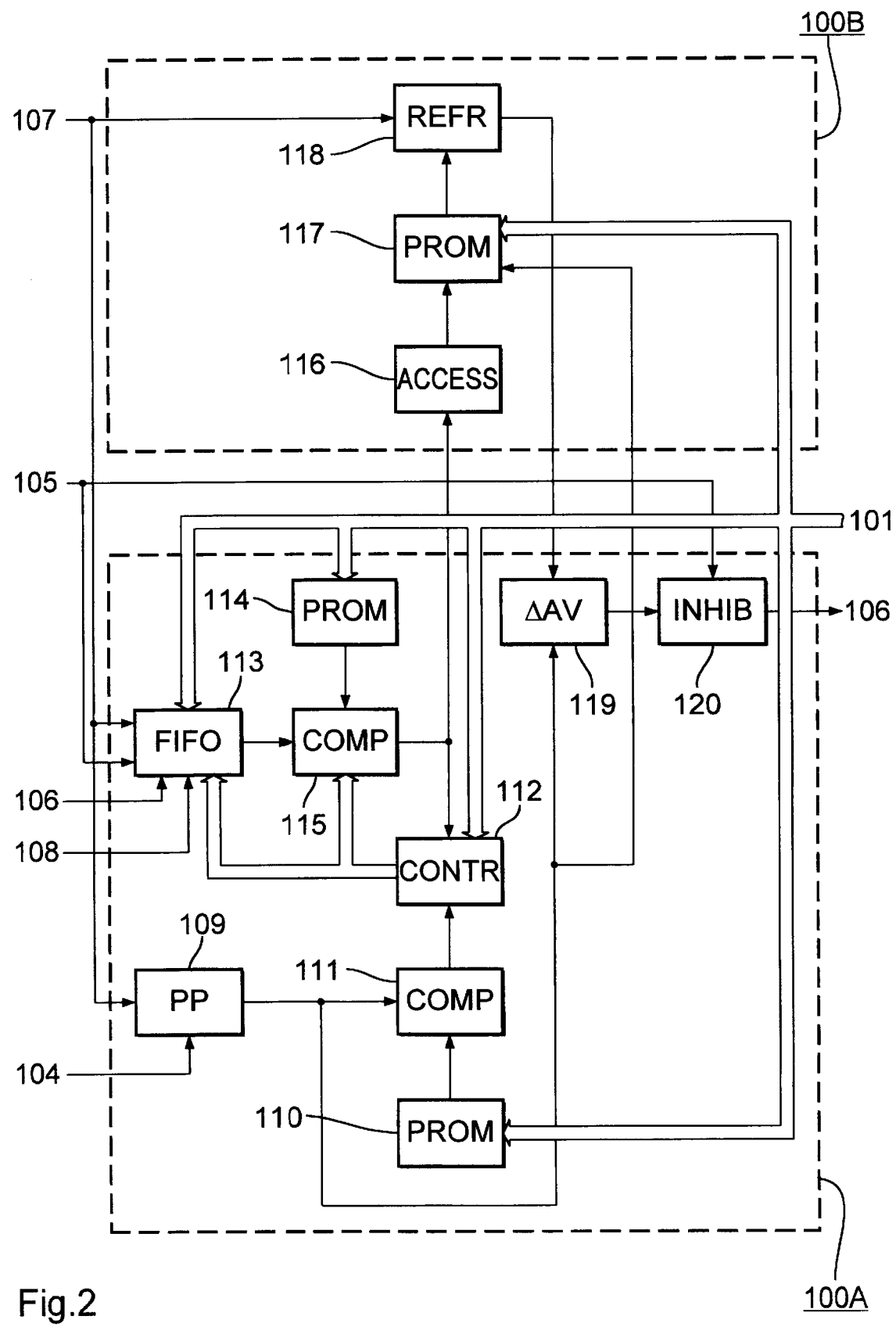

Advantageous modifications of the invention are otherwise characterized in the dependent claims or are shown in the following in further detail with the aid of the Figures, together with the description of the preferred embodiment of the invention. Shown are in:

FIG. 1 A general operational block diagram for a two-chamber pacemaker according to a preferred embodiment of the invention;

FIG. 2 An operational block diagram of a preferred embodiment of the stimulation control unit and the refractory switching means of the two-chamber pacemaker according to FIG. 1.

The basic diagram in FIG. 1 shows the components of a pacemaker arrangement, essential for explaining the invention, which components comprise a two-chamber pacemaker 100, a programming device 200, as well as an atrium electrode EA in the Atrium A and a ventricular electrode EV in the ventricle V of a heart H. In order to link the implanted pacemaker 100 to the programming device 200, an internal telemetric unit 101 is provided while a stimulation control unit 100A is provided for the general operational control. An internal program memory 102 and a data memory 103, as well as a pulse and timing generator 104 are assigned in the standard way to the latter. The ventricular electrode EV is connected on the input side to a ventricular sensing unit 105 and on the output side to a ventricular stimulation unit 106. In an analog manner, the atrium electrode EA is connected on the input side to an atrium-sensing unit 107 and on the output side to an atrium stimulation unit 108. The sensing units 105, 107 are connected—at least indirectly—with data inputs of the stimulation control unit 100A. The stimulation units 106, 108 are connected to control signal outputs of the same.

Apart from additional possible operating modes, which are of no further interest in connection with the invention, the two-chamber pacemaker 100 is designed for an atrium-synchronous chamber-stimulation operation. Furthermore, the pacemaker is designed (again in a manner known per se) to be switched from the 1:1 atrium-synchronous operation to an operating mode, which in principle can be referred to as pacemaker-VES-behavior, and to be switched back to the 1:1 synchronous operation at the end of such an episode of more frequent VES or atrial fluttering. The special feature of the suggested solution is that its design and operation permit an early switching back, specifically of the stimulation control unit 100A and the refractory switching means 100B.

The switching back in principle becomes possible as soon as an uninterrupted sequence of ventricular sensory events and refractory atrial sensory events is detected for a predetermined number of heart cycles.

FIG. 2 shows a block diagram of function elements for a preferred embodiment of the stimulation control unit 100A and the refractory switching means 100B of the two-chamber pacemaker 100 according to FIG. 1. The representation is limited to the functions essential for realizing the invention since the design and functions of a two-chamber pacemaker are known per se to the person skilled in the art.

The stimulation control unit 100A comprises first of all a stage 109 for determining the atrium rates, which stage is connected on the input side to the atrial sensing unit 107 and also to the timer 104. It furthermore comprises a programmable atrium-rate threshold value memory 110 and an atrium-rate comparator 111 that is connected on the input side to the stages 109, 110. The output of comparator 111 is connected to the input of a controller 112. The refractory time reversal function as a test, which is described in the following, can be triggered by these functional groups (among other things), as soon as the atrium rate drops again below a programmed threshold value, following a tachycardia episode.

This function is carried out by a signal sequence memory 113 that is connected to the atrium sensing unit 107 and the ventricle sensing unit 105, in cooperation with a signal pattern memory 114 and a comparator 115, which is connected to the outputs of both memories. The signal sequence memory 113 is a unit that is basically organized according to the FIFO principle and is provided with processing functions. Following activation via the controller 112, this memory sequentially stores signals coming from the atrium-sensing unit 107 and the ventricle sensing unit 105 by assigning an identification "As(ref)" (refractory atrium sensory event) or "Vs" (ventricular sensory event), insofar as these do not have to be classified as evoked signals with the aid of additional signals, which are received via signal connections to the ventricular stimulation unit 106 and the atrial stimulation unit 108.

As soon as the signal sequence memory 113 is full, meaning it contains the number of actually detected atrial and ventricular signals that are specified by its available capacity, the controller will trigger in the comparator 115 a pattern comparison of the memory content and the content of the signal pattern memory 114. With respect to the number of signals, the recorded and the stored signal patterns coincide by definition. Given a positive result of the comparison, meaning if the signal sequences coincide as well, the comparator unit 115 emits a signal which, on the one hand causes the controller to end the task and, on the other hand, travels to a memory access control 116 that belongs to the refractory switching means 100B. This control reverses the valid memory area in a refractory time memory 117, thereby adjusting a shortened refractory time (e.g. 200 ms instead of previously 400 ms) in a refractory time element 118 that is controlled by the memory 117. However, if the comparison result is negative (signal sequences do not coincide), then the input signal arriving next at the signal sequence memory 113 must be awaited and this signal—by ignoring the "older" signal—is then stored and a new comparison rim automatically, etc.

A signal coming from the atrial sensing means 107 travels via the refractory time element 118 to the stimulation control stage 100A, that is to say (in simple words) to an AV delay element 119. There, an AV time is started for which the value is adjusted in dependence on the actual atrial rate as a result of the output signal of the atrium rate determination stage 109, which is supplied via a control input. After passing through an inhibition stage 120 that is activated by a possible signal from the ventricular sensing means, the output signal from the AV delay element 119 finally triggers a ventricular stimulus of the ventricular stimulation stage 106, provided no spontaneous ventricular action is detected prior to the completion of the valid AV time. In dependence on the result of the aforementioned signal sequence comparison, the stimulation control occurs by maintaining the normal refractory time or adjusting a shortened refractory time. As a result of this, an early return to the 1:1 atrium-synchronous operation is possible if the comparison criterion is met, meaning even for rate values where the pacemaker normally would maintain the pacemaker VES behavior.

The described function for the most part can be programmed with respect to the concrete parameters, e.g. as symbolized in the Figure by the data link between the internal telemetric unit 101 and the units 110, 112 to 114 and 116. As a result of this, it is possible to selectively program the concrete test sequence, the atrium-rate threshold value, the signal sequence lengths and the refractory times. The latter can also be adjusted optionally in dependence on the atrium rate, as shown in the Figure through the connection between units 109 and 117.

The realization of the invention is not limited to the above listed, preferred exemplary embodiments. Rather, a number of variations are possible, which make use of the illustrated solution, even if the embodiments are different.

Thus, a number of the described functions can be realized with software-type solutions, while the use of special hardware solutions, e.g. ASICs, is possible as well. The above-mentioned storage means can also be realized by combining logic elements, if necessary with counters. For example, it makes sense to realize the cooperation of the signal pattern memory, the signal sequence memory and the associated comparator means in this way by using logic stages together with a programmable counter.

The above-mentioned programming options are not necessarily used for each embodiment. On the other hand, naming them does not exhaust the subject.

Ending of the pacemaker VES behavior, as described in the above, by returning to the 1:1 atrium-synchronous chamber stimulation must be viewed as preferred application case for the invention. Generally, the area of application of the invention extends to all cases where a shortening of the atrial refractory time and/or the post-ventricular atrial refractory time is intended to have the effect of changing refractory A-sensory events to non-refractory A-sensory events. An algorithm of this type can be used, for example, for terminating certain tachycardia conditions, which are created through a "circulating" excitation (so-called re-entry tachycardia conditions) by including the atrium and chamber (e.g. the so-called WPW syndrome). Thus, it is known, for example, that such tachycardias under certain conditions prevent and/or terminate synchronous chamber stimulation with short AV time through p-waves. For example, if a patient with WPW syndrome experiences a circulating excitation including the atrium and chambers via the AV node and an additional conduction path, the atrioventricular and ventriculoatrial conduction times can be such that the atrium depolarizations represent refractory A-sensory events and can therefore not trigger a chamber pulse. By shortening the (post-ventricular) atrial refractory time, it is then achieved that the atrium depolarization, which participates in the circulating excitation, is rated as non-refractory A-sensory event, that it can trigger a chamber pulse and that it can terminate the circulating excitation.

What is claimed is:

1. Two-chamber pacemaker (100), comprising:
   atrium sensing means (EA, 107) for sensing electrical activity in the atrium (A) and ventricle sensing means (EV, 105) for sensing electrical activity in the heart chamber (V) of a heart (H) and for emitting corresponding output signals,
   refractory switching means (100B) for influencing the processing of output signals of the atrium sensing means for a predetermined refractory period, following the appearance of an output signal from the atrium or the ventricle sensing means,
   ventricle stimulation means (106, EV) for generating stimulation pulses and the transmitting of these pulses to the ventricle and
   a stimulation control unit (100A) for controlling the time when the stimulation pulses are emitted,
   characterized in that
   a signal pattern memory (114) is provided for storing a signal sequence pattern, which reflects a predetermined sequence of heart activities, or a predetermined number of specified activities,
   a signal sequence memory (113) is provided for storing a sequence of output signals from the atrium sensing means and the ventricle sensing means,
   comparator means (115) are provided for comparing a sequence of output signals with the stored signal sequence pattern or the number of predetermined activities and for emitting an output signal if the two coincide, and
   refractory changeover means (116) are provided for adjusting a shortened refractory time for the refractory switching means in dependence on the output signal from the comparator means.

2. Two-chamber pacemaker according to claim 1, characterized in that the refractory switching means (100B) comprise a refractory time memory (117) with at least two storage areas for storing different refractory times, wherein respectively at least one of two storage areas can be accessed selectively by the refractory time changeover means (116).

3. Two-chamber pacemaker according to claim 1, characterized in that the refractory time changeover means comprise a divider stage with predetermined dividing ratio.

4. Two-chamber pacemaker according to claim 1, characterized in that the signal pattern memory (114) for storing a signal sequence pattern, representing a predetermined number of alternately occurring ventricular sensory events and refractory atrial sensory events, as well as the signal sequence memory (113) are designed for storing a number of output signals from the atrium sensing means and the ventricle sensing means (105, 107), which correspond to the length of the signal sequence pattern.

5. Two-chamber pacemaker according to claim 4, characterized in that the signal pattern memory (114) is designed for programming the length of the signal sequence pattern and that the signal sequence memory (113) is designed for a corresponding programming of the number of output signals over a telemetric distance (101, 200).

6. Two-chamber pacemaker according to claim 1, characterized in that the refractory switching means (100B) are designed to form a combined refractory time from a basic refractory time and an extension amount, which is added in case the refractory time is started by a signal from the ventricle sensing means (105).

7. Two-chamber pacemaker according to claim 2, characterized in that the refractory switching means (100B) are designed to determine the refractory time in dependence on an acquired frequency of the activity in the atrium.

8. Two-chamber pacemaker according to claim 1, characterized by test control means for activating the signal sequence memory (113) or the comparator means (115) in dependence on an acquired frequency of the atrium activity.

9. Two-chamber pacemaker according to claim 8, characterized in that the test control means comprise an atrium-rate determination stage (109) and an atrium threshold value memory (110), an atrium rate-comparator (111) that is connected to these two on the input side, as well as a test triggering stage (112) that is connected to the output of the atrium-rate comparator unit.

10. Two-chamber pacemaker according to claim 1, characterized in that the stimulation control unit (100A) is designed to be switched from a non-atrium synchronous 1:1 operating mode to an atrium-synchronous 1:1 operating mode, in dependence on signals from the atrium sensing means (EA, 107) that are influenced by the refractory switching means (100B).

* * * * *